United States Patent

Biancalana et al.

[11] Patent Number: 4,552,163
[45] Date of Patent: Nov. 12, 1985

[54] CLEANING DEVICE FOR DENTAL INSTRUMENTS TO BE USED DURING SURGERY AND DENTAL TREATMENTS

[75] Inventors: Carlo Biancalana, Perugia; Giuseppe Vescovi, Pregassona; Maurizio Volpini, Varese, all of Italy

[73] Assignee: Bitiess Microtecnica S.A., Switzerland

[21] Appl. No.: 519,907

[22] Filed: Aug. 3, 1983

[51] Int. Cl.⁴ .............................................. B08B 3/00
[52] U.S. Cl. .................................. 134/100; 134/56 R; 134/199; 422/292
[58] Field of Search .................. 134/56 R, 198, 57 R, 134/199, 100, 47; 206/368; 422/292, 300; 433/77

[56] References Cited

U.S. PATENT DOCUMENTS

| 3,041,212 | 6/1962 | Booth | 134/57 R |
| 3,220,424 | 11/1965 | Nelson | 134/47 |
| 4,285,352 | 8/1981 | McMahon et al. | 134/100 |
| 4,327,060 | 4/1982 | Nisii | 422/300 |

FOREIGN PATENT DOCUMENTS

| 506929 | 11/1954 | Canada | 134/56 R |
| 3005493 | 8/1981 | Fed. Rep. of Germany | 134/56 R |
| 316031 | 7/1929 | United Kingdom | 134/198 |

Primary Examiner—Stephen Marcus
Assistant Examiner—Renee S. Kidorf
Attorney, Agent, or Firm—Wigman & Cohen

[57] ABSTRACT

A cleaning device to be used during dental surgery and dental treatments for cleaning, disinfecting and drying instruments, in particular turbine drills, comprising a box-container, including a vertical cylindrical chamber delimited by a tubular body, provided with an opening in the top wall of said container, body which is formed by three coaxial elements assembled to each other and which can be disassembled. The chamber is barred at the bottom by a removable grate which is designed to support the instrument during the cleaning operations, which are performed by means of jets of pressurized water and air fed through nozzles, while lower nozzles deliver pressurized air containing a nebulized disinfectant. The discharge of dirty water used for washing is carried on through the waste-pipe and is promoted by at least one jet of pressurized air, which creates a suction effect towards the bottom of the chamber and at the same time prevents drops from coming out through the opening. The mixture of air and disinfectant is obtained by an atomizing unit in which disinfectant is supplied by means of a disposable spray bomb, with an airtight closure.

7 Claims, 4 Drawing Figures

CLEANING DEVICE FOR DENTAL INSTRUMENTS TO BE USED DURING SURGERY AND DENTAL TREATMENTS

BACKGROUND OF THE INVENTION

The present invention relates to a device to be used in dental or similar surgery, in order to receive, clean, disinfect and dry dental instruments, in particular turbine drills automatically, and thus eliminate various residues, like blood, so that the surgeon may find the instruments automatically cleaned, disinfected and dried, every time he picks up the instruments during surgery or dental treatments. Various types of devices are already known which deal with the cleaning and/or the sterilizing of dental or surgical instruments, but the majority of these require first of all the disconnection of the instruments, dental or surgical, as well as a much longer and complex operational cycle therefore said devices can only be used during the closure times of a dentist surgery.

SUMMARY OF THE INVENTION

The present invention aims at solving different problems, providing a device for cleaning, drying and disinfecting dental instruments, during surgery and dental treatments, and within the short interval in which the dentist introduces the instrument in its proper support between one phase of surgery and the following one. In this case the operator will use, as a support the washing chamber, incorporated in the device. Said cleaning, disinfecting and drying operations take place, according to a programmed sequence, which is initiated automatically as soon as the instrument is inserted in the device of the invention, providing a short operative cycle, but one of absolute reliability. The psychological effects on patients in seeing that the instruments used are always clean is remarkable, as many patients are sensitive to instruments on which blood and/or various residues due to surgery are adhered. The control of the starting of the cleaning operations is automatic, due to the presence of sensing means, in particular photoelectric cells, which control the introduction of the instrument in the treatement chamber and which automatically control the beginning of the program chosen for cleaning, which includes the washing of the instrument by strong jets of pressurized water and air directed against the instrument and the following disinfection with simultaneous drying by jets of pressurized air with the addition of atomized disinfectant of the kind which has a rapid action. The disinfection and drying phase begins simultaneously with the washing phase which can have a duration of 8 seconds only, while the disinfection and drying phase continues up to the completion of the whole cycle which has a duration of about 30 seconds. The device is programmed so that the operative cycle will be completed in a short time and accurately.

The device is built also in order to allow it to perform, at intervals and in a short time, a rapid disassembling of the parts that form the treatment chamber for their periodic accurate cleaning. In the same way the invention provides that the disinfectant used is supplied by means of a disposable container with airtight closure, especially conceived in order to avoid the use of unsuitable disinfectants.

Moreover, sensing means are provided to immediately signal if the disinfectant is running out, in order to allow the replacement with a new full container, so that any carelessness of the operator in checking the presence of disinfectant and in assuring the perfect efficiency of the device in time, can be avoided. As the signaling device becomes operative, a switch opens, stopping the operation of the apparatus until the recharge of the disinfectant medium has been completed.

BRIEF DESCRIPTION OF THE DRAWINGS

These and other characteristics and advantages of the device according to the invention will be better understood from the following description of an embodiment of the invention, taking in consideration the accompanying drawings, in which.

DETAILED DESCRIPTION OF THE PREFERRED EMBODIMENT

Figure 1:
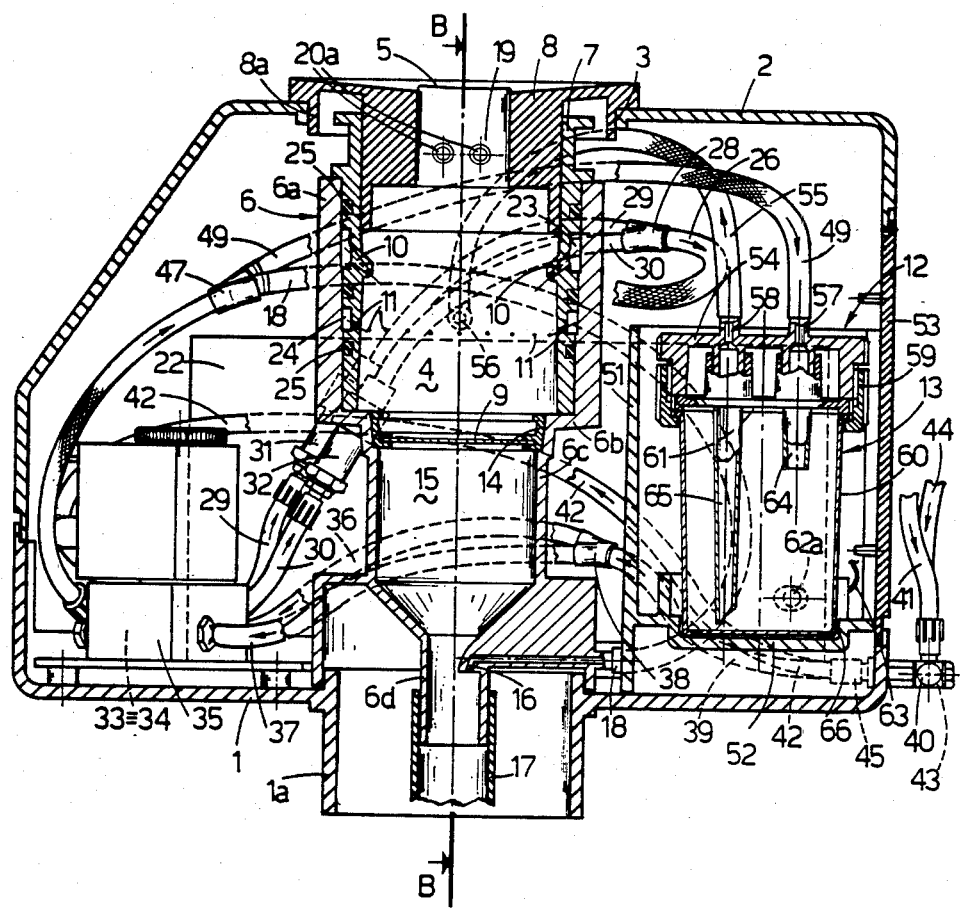
FIG. 1 is the vertical, longitudinal section of the device, taken on the line A—A of FIG. 2.

The device in question comprises a box-like outer container, comprising a base portion 1, supporting all the main components of the device, in the lower part of which a wide pipe union 1a is arranged for the waste-pipe 17, while the upper part of the container includes a shaped removable covering element 2, in the upper wall of which a circular orifice 3 has been obtained, coaxially to the washing, disinfecting and drying chamber which is substantially cylindrical and which is obtained inside a tubular body, formed by the combination of three tubular elements, coaxial to chamber 4 and mounted one into the other, in a manner capable of being disassembled and precisely by a tubular external body generally indicated with 6, which, starting from the top, includes a first portion 6a, which is substantially as high as the chamber 4 itself and which houses inside it a tubular body 7, which can be removed from the top. Said body 6a becomes narrower in correspondence with the bottom of the chamber 4 in the portion 6b, in which a shaped shoulder 14 is arranged, and is designed to receive a removable grate-shaped frame 9, which constitutes the perforated bottom of the chamber 4. Said grate 9 serves as a supporting means for the instrument which will be introduced in the chamber 4 from the top, and, at the same time, serves to retain the biggest residues removed from the instrument and which could obstruct the waste-piping. Underneath said grate 9 the body 6 forms a narrower section 6c, in which a tubular pipe 15 is obtained and, which is connected to the discharge pipe union 6d in which a nozzle 16 is provided, opening towards the bottom and in which pressurized air is blown out, which is fed through a pipe 18. The air entering into the pipe union 6d creates a jet directed towards the bottom, that, for induction, creates a suction effect in the outlet 6d, in the pipe 15 and in the chamber 4, which is what is necessary to promote the discharge of products from the washing operation of the instrument and at the same time also sucks towards the bottom any drop, which could be produced, during the treatment, thus preventing drops containing impurities, from getting out of the device and depositing on the instruments or on other things in the surroundings. On the pipe union 6d the end portion of the waste-pipe 17 is mounted, which is connected to the draining network, and comes out of the device through the outlet 1a.

Figure 2:
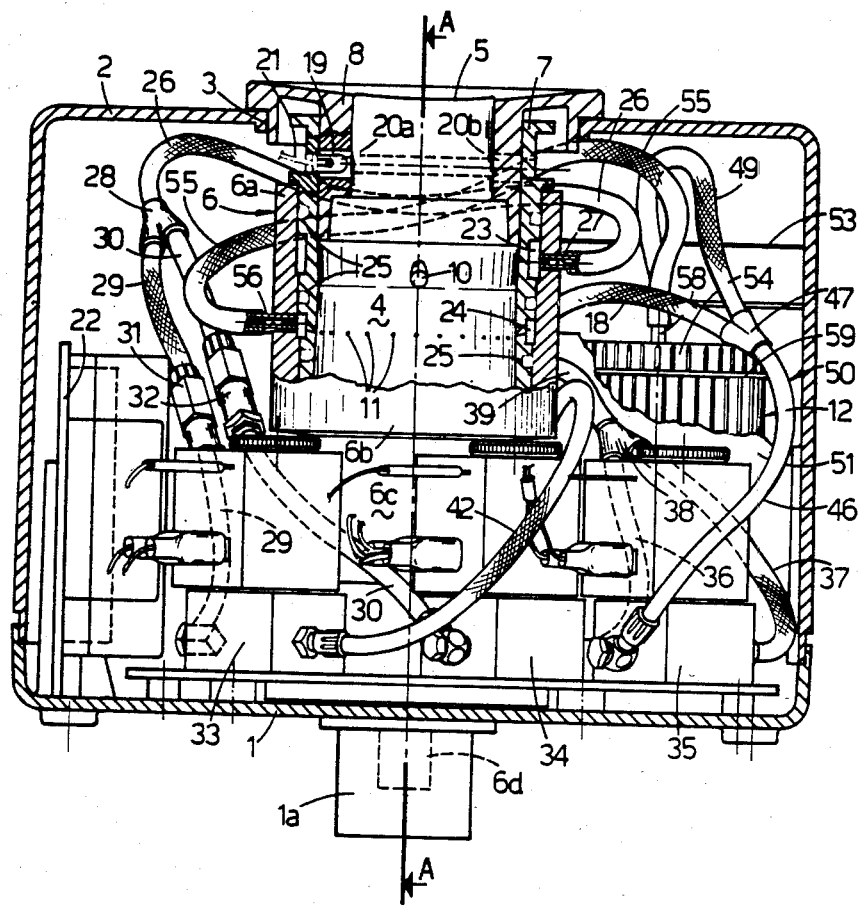
FIG. 2 is the vertical cross section, taken on the line B—B of FIG. 1.
Figure 3:
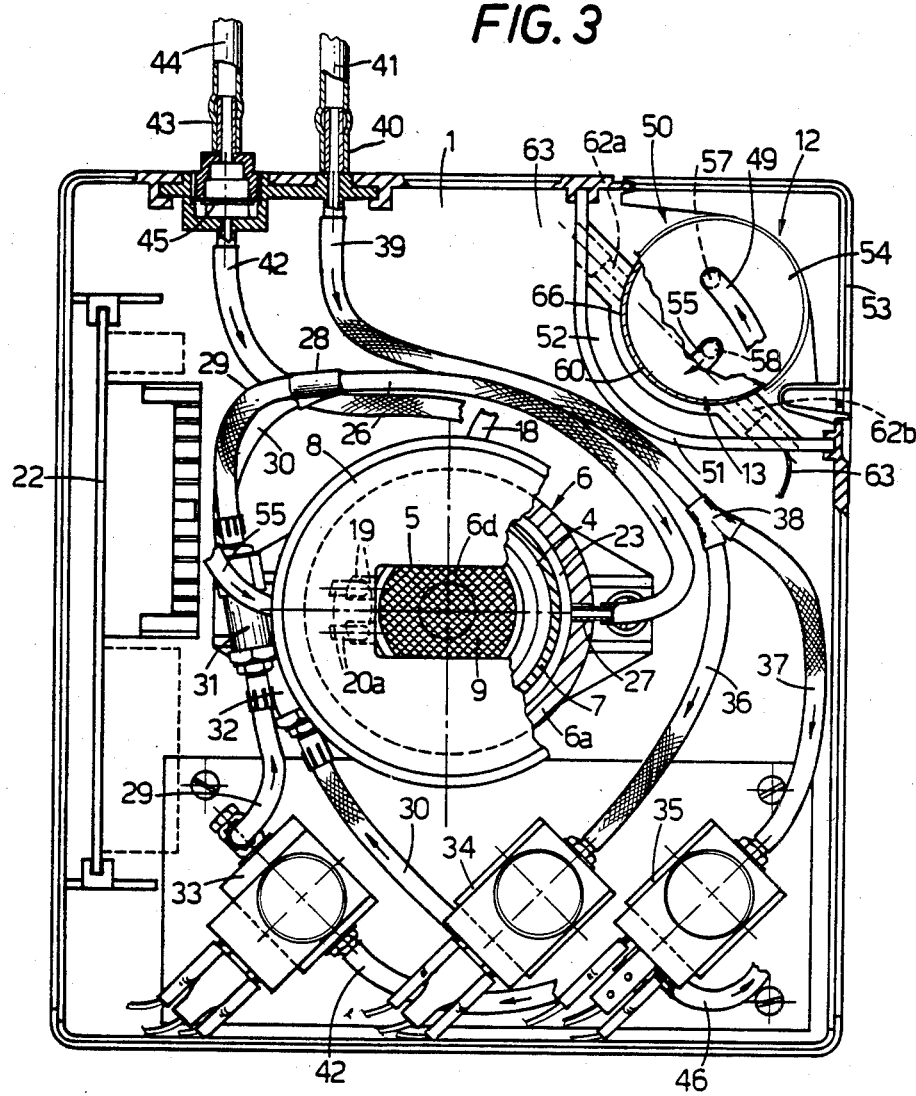
FIG. 3 is a diagrammatic top view of the inner most important components of the device after having removed the upper covering wall of the container box.
Figure 4:
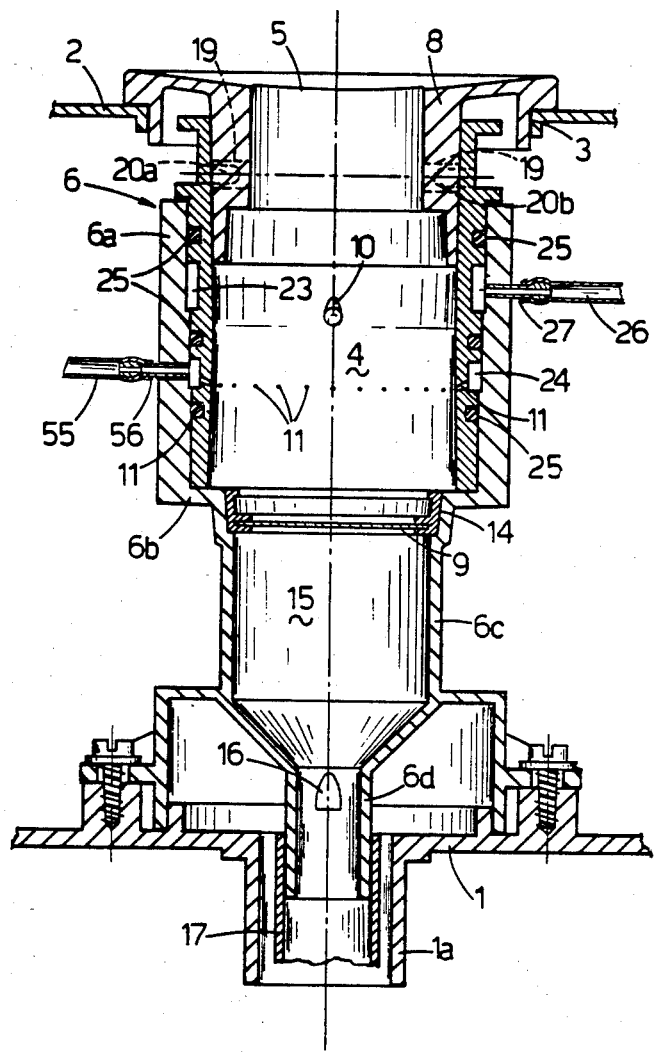
FIG. 4 is the detail of the whole section of the body, which defines the treatment chamber, section which in FIG. 2 is only partially shown.

On the upper part of the element 7 a mouth pipe 8 is inserted by pressure, and is fitted in with its peripheral edge 8a in the orifice 3 of the covering member 2. The mouth pipe 8 forms an opening 5 to chamber 4, preferably of a rectangular cross section. In the side wall of the mouth pipe 8, and precisely in the area adjacent to the upper portion of the element 7, two pairs of coaxial orifices 19 are provided, through which pass the rays produced by the two pairs of transmitting elements 20a, 20b or photoelectric cells, inserted in the lateral wall of the member 8, and which are connected to a circuit 21. Said photoelectric cells 20a, 20b (FIG. 2) create a ray for screening the entrance conduit 5, said rays being interrupted by introducing the instrument in chamber 4 and that in response, a control means makes operative a programming-timing unit 22, which controls at predetermined time intervals and with predetermined durations, the operations of the various components of the device, stopping them after they have completed their function.

The tubular body 7 can easily be obtained advantageously by a molding process with plastic material, and has an internal surface substantially cylindrical, while externally it has two wide coaxial annular grooves, which in correspondence with the internal surface of the body 6, form respectively two annular manifolds 23 and 24, and smaller annular grooves adjacent the previous ones are designed to receive sealing rings 25. In correspondence with the first manifold 23, in the lateral wall of the unit 6a of the body 6 at least one pipe union 27 is arranged for the connection of the pipe 26 conveying pressurized air and water, while in the wall of the body 7, in correspondence with the manifold 23, at least two nozzles 10, are provided which are directed so that they can create powerful jets of pressurized air and water, directed towards the bottom and towards the axis of the chamber 4, in the zone where the instrument to be cleaned is placed. Pipe 6 receives the mixture of air and water through the pipe-union 28, to which pipe 29 is inserted for the supply of water, and which includes a check valve 31 and the pipe 30 for the supply of air, in which another check valve 32 is inserted. The pipes 29 and 30 are connected respectively to the electro-valves 33 and 34, which are controlled by the programming unit 22. The electro-valves 33 and 34 and the check valves 31 and 32 could be also inserted in a sole assembly comprising a water-air mixing unit controlled by a single electro-valve. A third electro-valve for the control of the supply of the pressurized air feeding the atomizer 12 is indicated with 35.

The electro-valves 34 and 35 receive air through the pipes 36 and 37, which are branched off by means of the pipe union 38, from the supply pipe 39, which through the pipe union 40 is joined to pipe 41 which connects this latter to an air compressor (FIG. 1). On the contrary the electro-valve 33 receives pressurized water from pipe 42, which is connected to pipe union 43, to which the water supply pipe 44 is connected with the interposition of a filter 45. From the electro-valve 35 (FIG. 2) comes out a pipe 46, which through the pipe union 47 conveys pressurized air to pipe 18 which feeds the nozzle 16, as well as to the pipe 49, which feeds the atomizing unit generally indicated with 12. Said atomizer unit 12 is mounted, in a removable manner, in a space 50 delimited by lateral walls 51, by a door 53 and by a bottom wall 52, space which is obtained at one side of the container-box 1, 2.

The unit 12 includes a head 54, in which there are pipe-unions 57 and 58 for pipes 49 for adduction of air and for a pipe 55 from which the mixture of air and disinfectant comes out and which leads to the inlet 56 which supplies the manifold 24, which, in turn, supplies the nozzles 11 arranged in the body 7 dispensing the air, which carries out with it, in atomized particles, disinfectant for the disinfection and the drying of the instrument in chamber 4.

The head 54 is connected by a threaded nut 59 to a cylinder or container 13 of a disinfectant medium. Said container 13 is formed by a rigid element 60 with a bowl-like shape, with transparent walls, and is provided with an upper gripping flange 60a and is closed in the upper part by a rubber membrane 61. The reservoir 60 is placed in a housing recess 66, obtained in the bottom 52 of the chamber 50, in which the sensing means 62a, 62b are placed, inserted in a circuit 63 (not shown), comprising also an alarm sound and/or luminous means as well as a means for stopping the feeding of the circuits of the apparatus so as to prevent the operation of this latter until the recharge of the disinfectant has been carried out. The rays emitted by the elements 62a, 62b pass through the transparent wall of the reservoir 60 and are intercepted by the liquid container in it. When the liquid goes beneath a level lower than the one where the sensing means 62a, 62b, are provided, these latter detect the different situation and cause the alarm system to become operative. The connections 57 and 58, situated in the head 54, extend towards the bottom respectively with a short pipe 64, with a sharp edge, and with a pipe 65, also with a sharp edge, the latter being of a length sufficient for it to reach near the bottom of the reservoir 60, when the container 13 is mounted. For this purpose the container 13 is put closer to the head 54 by pushing hard the head towards the membrane 61, so that the small pipes 64 and 65 can penetrate through the membrane 6 and reach the inner cavity of the reservoir 60, which becomes the atomizing chamber. In fact from the small pipe 64 pressurized air which bubbles in the disinfecting liquid, flows in and therefore the air, which drags with it particles of said liquid, goes up again in the small pipe 65, escapes out of the connection 58, so as to enter the pipe 55 and to feed the nozzles 11. This device could be substituted with any other equivalent device adapted to carry out the same tasks. The operation of the device is therefore rather simple.

When the instrument is introduced into the chamber 4, the ray from cells 20a, 20b is interrupted, so that under the control of the photoelectric cells 20a, 20b, the operative cycle starts and the valves 33 and 34 open, thus providing pressurized air and water to the nozzles 10, so that pressurized air reaches nozzles 10. At the same time valve 35 opens, therefore the atomizer 12 starts to work and a flow of air containing disinfectant reaches the nozzles 11, while only air is conveyed to the nozzle 16. After the predetermined washing time, the electro-valves 33 and 34 close, said electro-valves 33, 34 and 35 being normally closed.

The ray screen created by the photoelectric cells 20a, 20b remains interrupted until the instrument is withdrawn from the cleaning device because a portion of the instrument support handle remains in the entrance conduit arranged in the tubular body while the instrument is being cleaned.

What is claimed is:

1. A device for cleaning, disinfecting and drying dental instruments, comprising:

a box-like container, in the upper part of which an entrance orifice is located;

a tubular body mounted below the entrance orifice, said body having a body orifice coaxial to the entrance orifice;

said body defining with its interior surfaces a substantially cylindrical treatment chamber;

a removable grate located at the bottom of the chamber;

a first series of nozzles dispensing a mixture of pressurized air and water into the chamber;

an atomizer unit for producing atomized disinfectant;

beneath the first series of nozzles is located a second series of nozzles which supply air mixed with the atomized disinfectant, the disinfectant being supplied by an airtight disposable cylinder;

said tubular body comprising a plurality of tubular coaxial members inserted one in the other, so that they can be disassembled;

wherein the outermost of said coaxial members comprises a first section substantially of the same length as the chamber and in which there is a second of said coaxial tubular members upon which is a third of said coaxial tubular members which has an opening that delimits the body orifice which is to be used for inserting the instruments into the chamber;

the outermost and second coaxial members having facing surfaces which form together a first manifold for receiving the mixture of pressurized air and water, which is dispensed through the first series of nozzles which extend through the second tubular coaxial member;

said facing surfaces also forming a coaxial manifold which receives the disinfectant mixed with air which is dispensed through the second series of nozzles which pass through the second coaxial tubular member;

a pair of sensing elements which produce photoelectric screening rays are mounted in the second tubular coaxial member adjacent openings in the third coaxial tubular member;

the rays form a barrier screen in the body orifice for detecting the presence of dental instruments;

a programming-timing unit being connected to and activated by said sensing elements;

the removable grate being located on a seat formed in said outermost tubular member;

a lower section of said outermost tubular member forms a waste pipe;

an air nozzle dispenses pressurized air into the waste pipe in the same direction in which the mixture flows from the chamber;

first supply pipes being connected to the first series of nozzles for supplying water and air to the nozzles;

first electro-valves for controlling the first supply pipes;

a second supply pipe for supplying pressurized air to the atomizer unit;

a second electro-valve for controlling the second supply pipe;

the electro-valves being normally closed and are opened according to a predetermined time and duration sequence by the programming unit.

2. A device according to claim 1, wherein on the facing surface of the second coaxial member are annular grooves which in combination with the facing surface of the outermost coaxial member of the tubular body form the manifolds.

3. The device according to claim 1, further comprising check valves inserted within the first supply pipes.

4. The device according to claim 1, wherein the atomizing unit further includes:

an upper head which is connected to the coaxial manifold by a pipe, said upper head being connected to the second supply pipe;

a transparent cylinder connected to the upper head in a manner capable of disassembly;

a short pipe extends from the upper head into the cylinder.

5. A device according to claim 4, wherein the atomizer unit is housed in a space on one side of the container;

said unit being accessible through a door in the container;

said space including a bottom portion which defines a housing for receiving the base of the cylinder;

on the sides of said housing are photocells connected to a circuit which comprises optical and/or acoustic signalling means which becomes operative when rays emitted by the photocells are no longer interrupted by the presence of disinfectant liquid in the cylinder, said photocells being mounted above the bottom of the cylinder.

6. A device for cleaning, disinfecting and drying instruments, comprising:

a housing having an opening at the top thereof;

a chamber mounted within the housing, the chamber having an opening coaxial and aligned with the housing opening;

first nozzle means for injecting a mixture of pressurized air and water into said chamber;

means for atomizing disinfectant;

second nozzle means for injecting a mixture of pressurized air and atomized disinfectant into said chamber;

a waste pipe connected to a lower portion of the chamber;

third nozzle means for injecting pressurized air into the waste pipe so as to induce a suction effect for promoting drainage from the chamber through the waste pipe;

electronic means for sensing the presence of an instrument in said chamber; and means for automatically controlling the operation of the injecting means in response to the sensing means.

7. The device according to claim 6, further comprising:

means for storing disinfectant;

means for mixing the disinfectant with pressurized air;

means for sensing the presence of disinfectant in the storing means; and means for providing a signal to the controlling means in response to an absence of disinfectant.

* * * * *